(12) United States Patent
Pantano

(10) Patent No.: US 10,543,012 B2
(45) Date of Patent: Jan. 28, 2020

(54) ULTRASONIC SURGICAL DEVICE WITH REDUCTION IN ELECTRICAL INTERFERENCE

(71) Applicant: MISONIX, INCORPORATED, Farmingdale, NY (US)

(72) Inventor: Salvatore Pantano, Farmingdale, NY (US)

(73) Assignee: MISONIX, INC., Farmingdale, NY (US)

(\*) Notice: Subject to any disclaimer, the term of this patent is extended or adjusted under 35 U.S.C. 154(b) by 242 days.

(21) Appl. No.: 15/664,663

(22) Filed: Jul. 31, 2017

(65) Prior Publication Data

US 2018/0036030 A1    Feb. 8, 2018

Related U.S. Application Data

(60) Provisional application No. 62/370,016, filed on Aug. 2, 2016.

(51) Int. Cl.
*A61B 17/32* (2006.01)

(52) U.S. Cl.
CPC .......... *A61B 17/320068* (2013.01); *A61B 2017/32007* (2017.08)

(58) Field of Classification Search
CPC ............ A61B 17/32; A61B 17/320068; A61B 2017/00106; A61B 2017/0011; A61B 2017/320069; A61B 2017/320073; A61B 2017/320082; A61B 2018/1293; A61B 18/14; H01L 41/042; H01L 41/044; B06B 2201/55; B06B 1/0207; B06B 1/0215; B06B 1/0261; B06B 1/0292; B06B 1/04; B06B 1/045; B06B 1/06
See application file for complete search history.

(56) References Cited

U.S. PATENT DOCUMENTS

| | | | | |
|---|---|---|---|---|
| 5,334,183 | A * | 8/1994 | Wuchinich | A61B 17/22012 600/104 |
| 6,251,110 | B1 * | 6/2001 | Wampler | A61B 17/32006 600/2 |
| 2004/0006269 | A1 | 1/2004 | Novak et al. | |
| 2009/0066192 | A1 * | 3/2009 | Taki | A61B 17/320068 310/354 |
| 2012/0116261 | A1 * | 5/2012 | Mumaw | A61B 17/00234 601/2 |
| 2014/0276770 | A1 | 9/2014 | Ellman | |
| 2015/0032022 | A1 | 1/2015 | Stone et al. | |

\* cited by examiner

*Primary Examiner* — Robert A Lynch
(74) *Attorney, Agent, or Firm* — R. Neil Sudol; Henry D. Coleman

(57) ABSTRACT

An ultrasonic surgical device has a hand piece, a probe, and an electromechanical transducer assembly disposed inside the hand piece. The probe is mounted to a distal end of the hand piece and is operatively connected to the transducer assembly. An electrical connector is mounted at least indirectly to the hand piece, while an electrical circuit electrically or operatively connects the probe to the electrical connector. A wire or cable is operatively coupled at one end to the electrical connector and at an opposite end to electrical ground.

6 Claims, 6 Drawing Sheets

ULTRASONIC SURGICAL DEVICE WITH REDUCTION IN ELECTRICAL INTERFERENCE

BACKGROUND OF THE INVENTION

This invention relates to ultrasonic surgical devices. The invention also relates to an associated surgical method. The invention is particularly useful in reducing electrical interference between the electromechanical energization system of an ultrasonic surgical device and intraoperative neurophysiological monitoring devices (IONM).

The ultrasonic removal of tissue as a result of direct instrument-target tissue contact is performed with the help of a hand-held device including a handpiece and any of a multitude of handpiece attachments or probes.

In the handpiece, a high voltage signal of a frequency equal to that of the resonant frequency of the handpiece-probe assembly is converted into mechanical vibratory motion. The electromechanical conversion is achieved by using either a magnetostrictive or piezoelectric stack. Typically a handpiece is fitted with a piezoelectric stack.

A piezoelectric stack can be built using one or more piezo-ceramic disks. The ceramic disks are sandwiched between electrodes which ensure an electrical connection to an ultrasonic generator via a handpiece cable.

Ultrasonic systems used for the removal of tissue located in the close proximity of critical structures that are part of the body's nervous system may use an electrical scheme where the piezoelectric stack is electrically isolated from the probe, the applied part. This is called a floating output and is done in order to minimize unwanted leakage currents that could negatively impact the nervous system. However it is noted that leakage current levels that are well within the limits defined by safety standards may create electrical interference with other devices within the surgical field. Such other devices include Intraoperative Neurophysiological Monitoring devices or IONM devices.

Intraoperative neurophysiological monitoring has been utilized in attempts to minimize neurological morbidity from operative manipulations. The goal of such monitoring is to identify changes in brain, spinal cord and peripheral nerve function prior to irreversible damage. Intraoperative monitoring also has been effective in localizing anatomical structures, including peripheral nerves and sensorimotor cortex, which helps guide the surgeon during dissection.

During the ultrasonic removal of tissue via direct probe-tissue contact, leakage currents, even when below the safe operating levels current could interfere with and prevent the proper operation of an IONM.

OBJECTS OF THE INVENTION

It is an object of the present invention to provide an improved ultrasonic surgical device which reduces or eliminates electrical interference with other electrical devices within the surgical field.

A more specific object of the present invention is to provide such a surgical device which reduces or eliminates undesired leakage currents.

A related object of the present invention is to provide a method for ultrasonic surgery wherein electrical interference between an ultrasonic surgical instrument and other electrical devices at or near the operating site is reduced if not eliminated.

These and other objects of the present invention will be apparent from the descriptions and drawings herein.

Although every object of the invention is attainable by at least one embodiment of the invention, there is not necessarily any single embodiment that achieves all of the objects of the invention.

SUMMARY OF THE INVENTION

The present invention provides a solution to unwanted interference in ultrasonic surgery. The invention basically consists of connecting the probe, which is the part of the instrument that is applied to or placed into contact with a patient's tissues, to earth ground. Comparative measurements between (a) a piezoelectric handpiece using a floating stack and a non-grounded probe and (b) a floating stack with a grounded probe have showed a substantial reduction, by approximately one order of magnitude, in leakage current flowing through the applied part. When tested with an IOMN system, previously unacceptable interference was replaced by a normal operating condition.

An ultrasonic surgical device in accordance with the present invention comprises a hand piece, a probe, and an electromechanical transducer assembly disposed inside the hand piece, the transducer assembly being configured for converting electrical waveform energy of an ultrasonic frequency into ultrasonic vibratory energy. The probe is mounted to a distal end of the hand piece and is operatively connected to the transducer assembly. An electrical connector is mounted at least indirectly to the hand piece, while an electrical circuit electrically or operatively connects the probe to the electrical connector. A wire or cable is operatively coupled at one end to the electrical connector and at an opposite end to electrical ground.

Where the transducer assembly includes a front driver, a stack of piezoelectric disks, a rear driver, and a bolt connecting the rear driver to the front driver, the electrical circuit includes the front driver, the bolt and the rear driver. Generally, all device components except the circuits for energizing the transducer elements may be connected to the grounding circuit.

A method for using the above-described ultrasonic surgical device comprises providing the wire or cable, operatively coupling one end of the wire or cable to the electrical connector and an opposite end to electrical ground, and placing an operating tip of the probe in contact with organic tissue of a patient. While the operating tip is in contact with the organic tissue, one conducts an alternating voltage to the transducer assembly to induce same to generate a mechanical standing wave of ultrasonic frequency in the probe. Simultaneously therewith, one conducts leakage current away from the probe to ground via the electrical circuit, the connector and the wire or cable.

The method further contemplates providing an intraoperative neurophysiological monitoring device, operatively connecting the intraoperative neurophysiological monitoring device to the patient proximate a point of contact of the operating tip of the probe with the organic tissue of the patient, and operating the intraoperative neurophysiological monitoring device to detect neuron activation.

DETAILED DESCRIPTION

Figure 1:
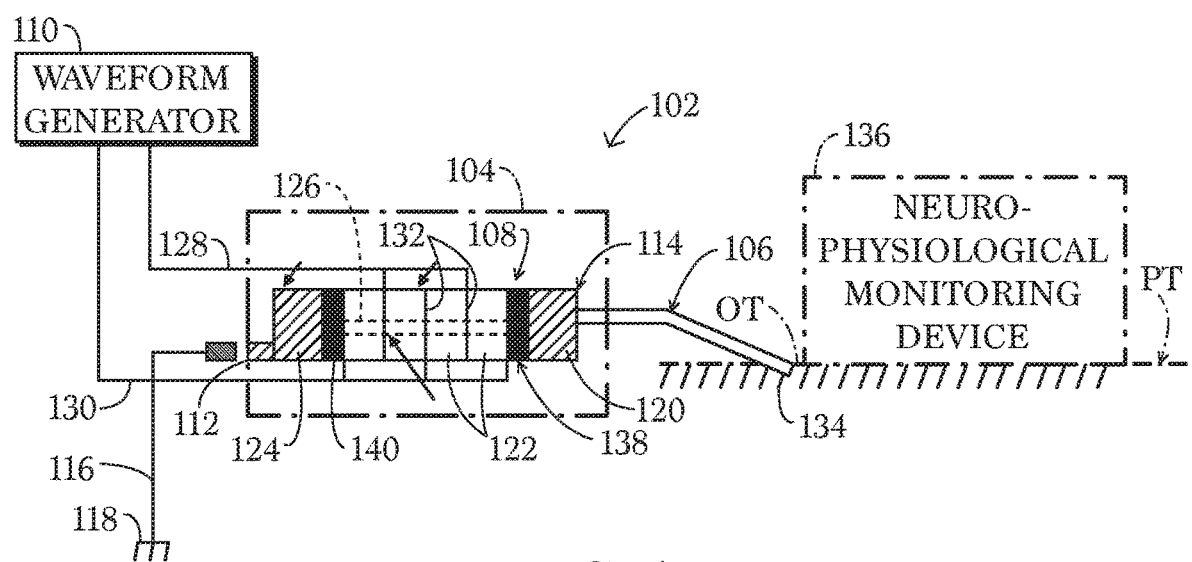
FIG. 1 is a diagram of an ultrasonic surgical system in accordance with the present invention, showing a blue monopolar cable connecting an ultrasonic surgical instrument or device to ground.

As depicted in FIG. 1, an ultrasonic surgical system comprises an ultrasonic surgical device 102 comprising a hand piece 104, a probe 106, and an electromechanical transducer assembly 108. The transducer assembly 108 is disposed inside the hand piece 104 and is configured for converting electrical waveform energy of an ultrasonic frequency from a waveform generator 110 into ultrasonic vibratory energy.

Probe 106 is mounted to a distal end of the hand piece 104 and is operatively connected to the transducer assembly 108. An electrical connector or spud, schematically indicated at 112, is provided at a rear or proximal end of the hand piece 104. An electrical circuit 114, including selected parts of the transducer assembly 108, electrically or operatively connects the probe 106 to the electrical connector 112. A wire or cable 116 is operatively coupled at one end to the electrical connector 112 and at an opposite end to electrical ground 118.

As described in U.S. Pat. No. 5,371,429, the disclosure of which is hereby incorporated by reference, transducer assembly 108 includes a front driver 120, a stack of piezoelectric disks 122, a rear driver 124, and a bolt 126 connecting the rear driver to the front driver. Electrical circuit 114 includes front driver 120, bolt 126 and rear driver 124. Generally, various components of device 102 may be included in or connected to the grounding circuit 114 except for the circuit elements that energize piezoelectric disks 122. Those circuit elements include leads 128, 130 and electrodes 132, some of which are located between adjacent piezoelectric disks 122, and two of which are located between respective piezoelectric disks 122 and insulator disks 138 and 140 respectively.

Insulator disks 138 and 140 serve to electrically isolate the stack of piezoelectric disks 122 from the probe 106, rendering the stack a floating output.

A method for using the above-described ultrasonic surgical device comprises providing the wire or cable 116, operatively coupling one end of the wire or cable to the electrical connector 112 and an opposite end to electrical ground 118, and placing an operating tip 134 of the probe 106 in contact with organic tissue OT of a patient PT. While the operating tip 134 is in contact with the organic tissue OT, one conducts an alternating voltage to the transducer assembly 108 from waveform generator 110 to induce the transducer assembly to generate a mechanical standing wave of ultrasonic frequency in the probe 106. Simultaneously therewith, one conducts leakage current away from the probe 106 to ground 118 via the electrical circuit 114, the connector 112 and the wire or cable 116.

The method further contemplates providing an intraoperative neurophysiological monitoring device 136, operatively connecting the intraoperative neurophysiological monitoring device to the patient PT proximate a point of contact of the operating tip 134 of the probe 106 with the organic tissue OT of the patient PT, and operating the intraoperative neurophysiological monitoring device 136 to detect activation or stimulation of the nervous system of the patient.

Transducer assembly 108 includes the two insulating disks 138 and 140 which are provided between the stack of piezoelectric or piezoceramic disks 122 and the front driver 120 and the rear drive 124, respectively. Insulating disks 138 and 140 serve to isolate the metal probe 106 from the disks 122 and the energization or voltage-application circuit elements 128, 130, 132. The present invention reduces or eliminates leakage currents that may nevertheless enter the patient through the probe 106 from the transducer assembly 108.

Figure 2:
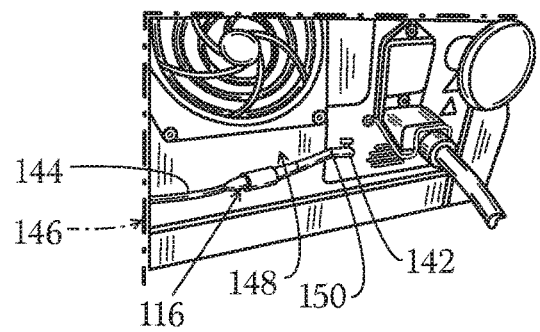
FIG. 2 is a partial view of a rear panel of a power console for the ultrasonic surgical system of FIG. 1, showing an end of the blue monopolar cable of FIG. 1 connected to a grounding terminal on the rear panel.
Figure 3:
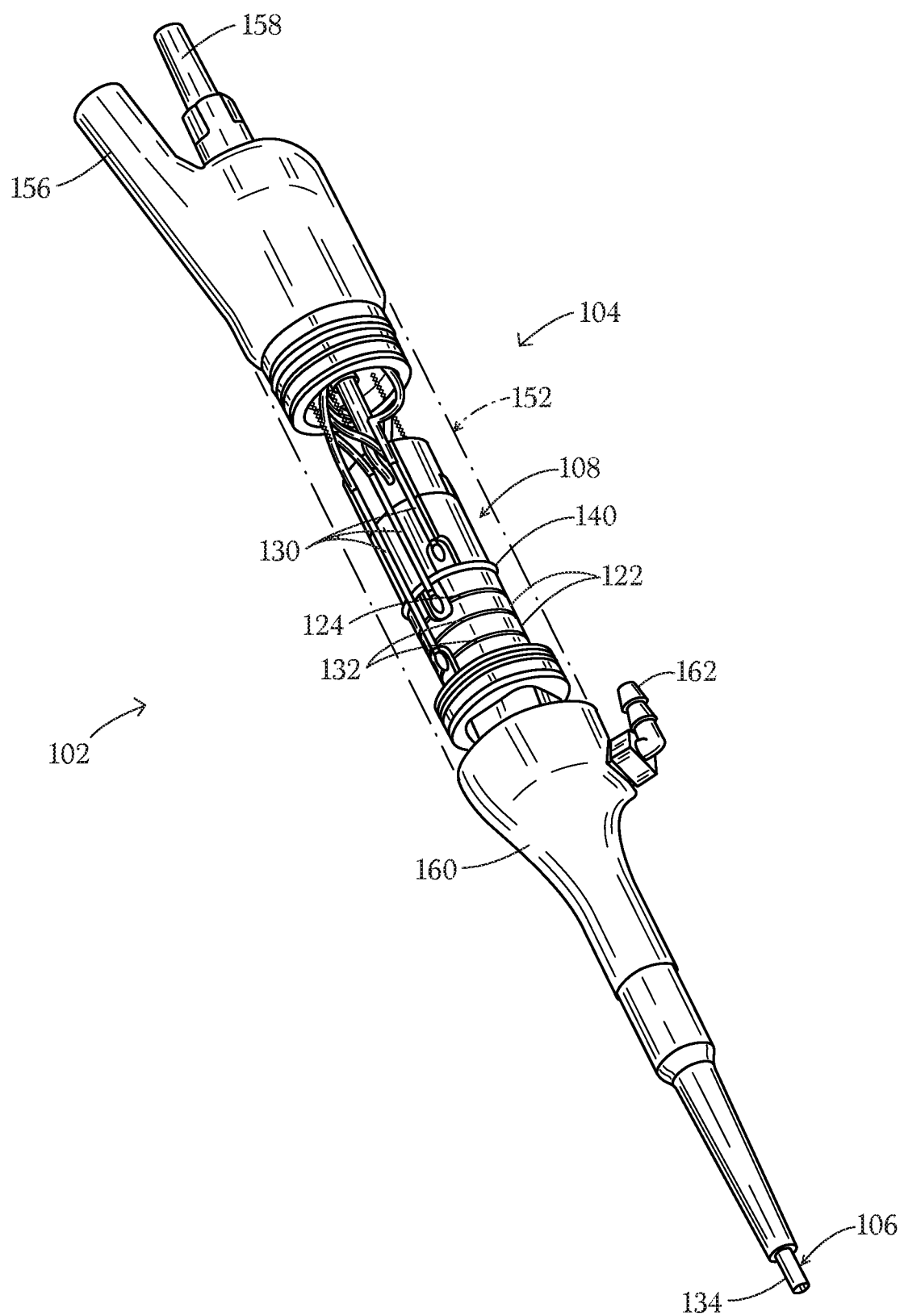
FIG. 3 is an isometric front and side view of an ultrasonic aspirator instrument in accordance with the invention, with a middle portion of a housing removed to show operative components.

Metal connector or spud 112 in the rear of the handpiece 104 is provided in prior art instruments to enable coupling of an RF cautery device so that probe 106 becomes a carrier for RF current. Wire or cable 116 may take the form of a blue monopolar cautery cable (part No. CFSM6-C130). Cable 116 is typically connected to ground 118 via a screw terminal 142 (FIG. 2) on a rear panel 144 of a power console or cabinet 146. In that case, an adapter or shunt member 148 is provided. Adapter or shunt member 148 is a pin insertable at one end into cable 116 and provided at an opposite end with an eyelet or loop 150 for insertion around the grounding screw terminal 142.

Figure 4:
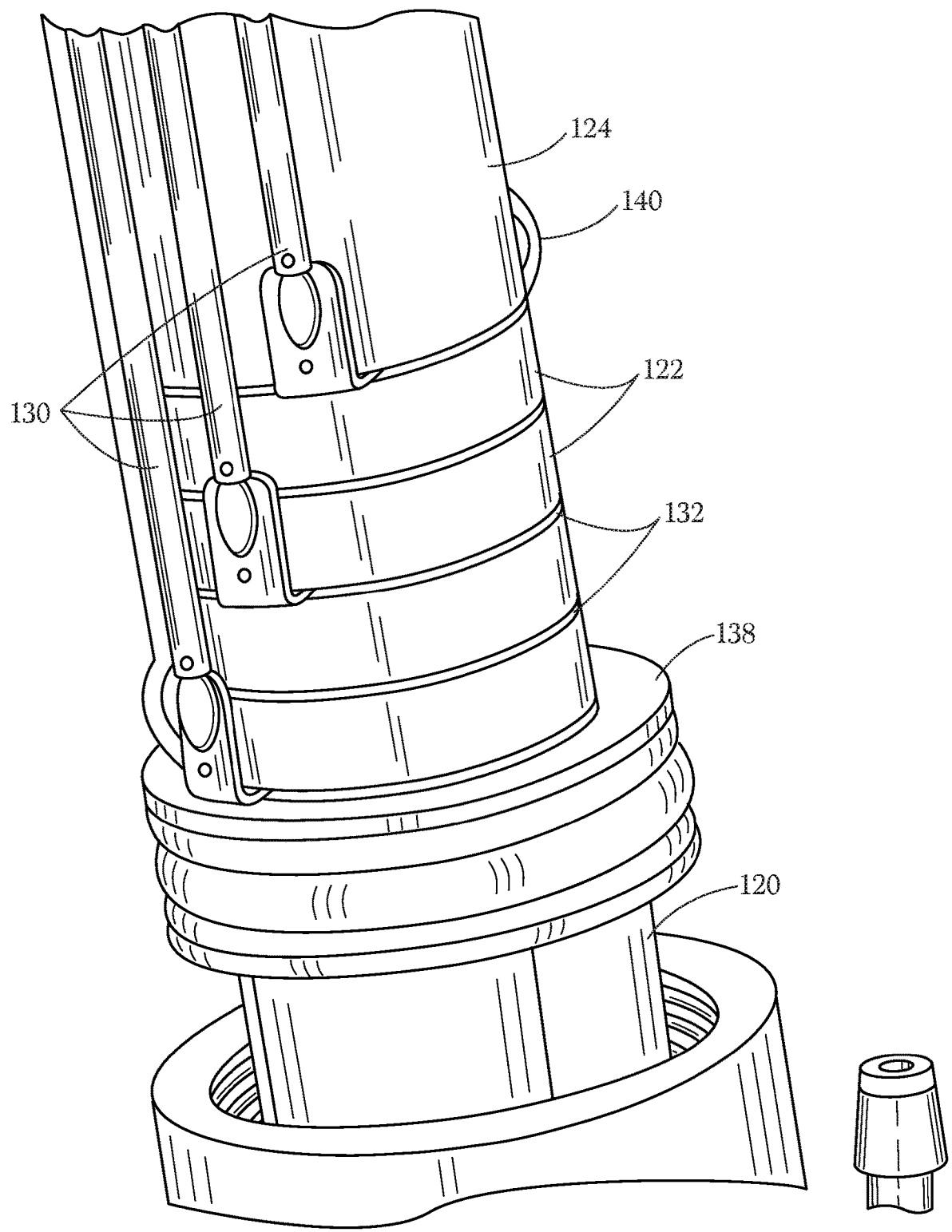
FIG. 4 is a detail view of the instrument of FIG. 3, on a larger scale.
Figure 5:
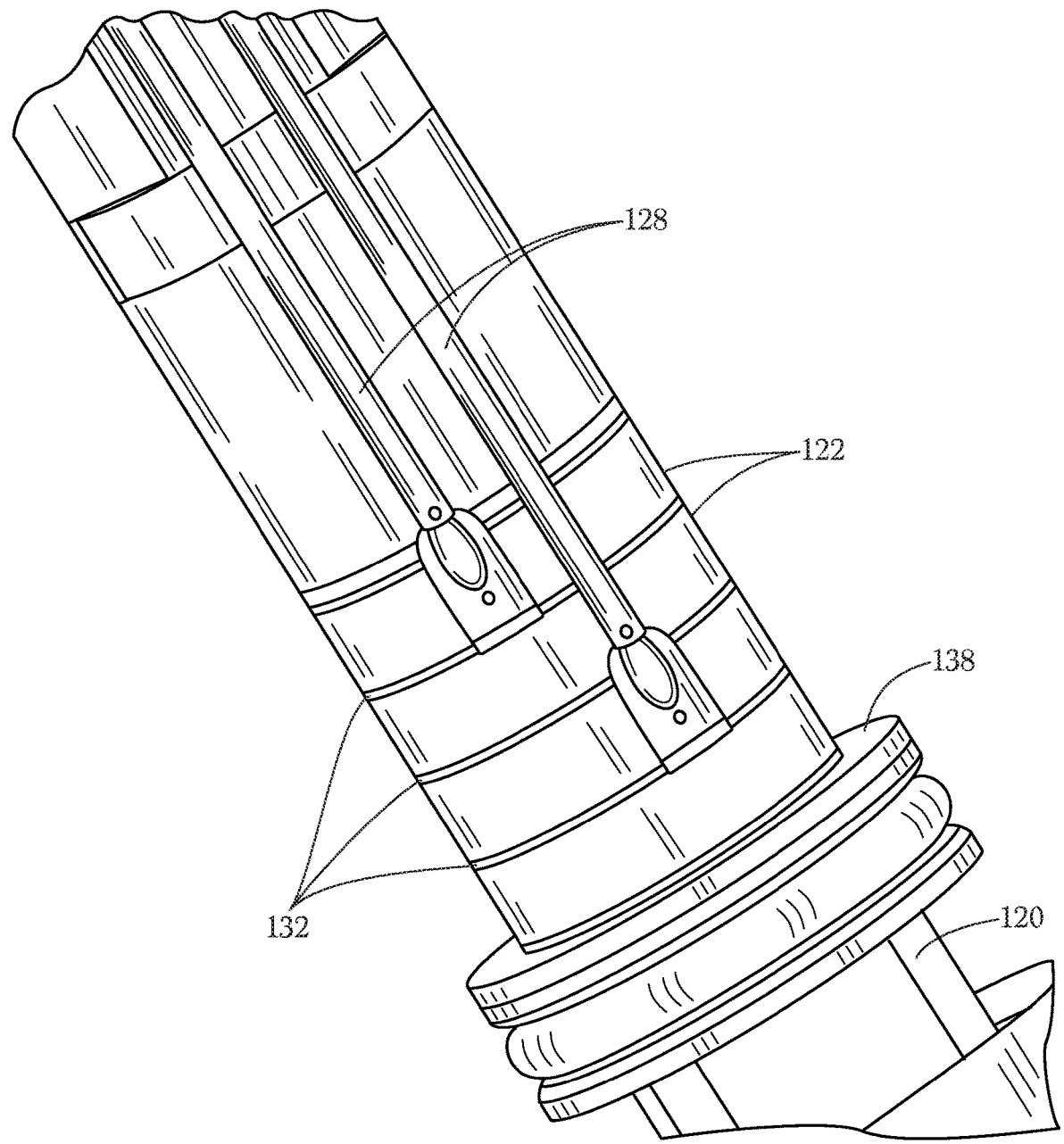
FIG. 5 is a detail view, similar to FIG. 4 but from another side of the instrument.

FIGS. 3-7 depict a particular embodiment of device 102 that is an ultrasonic aspirator particularly useful in neurological operations. The Sonastar FLV-12801 of Misonix Incorporated is such an aspirator. Parts illustrated in FIGS. 3-7 and discussed above bear the same reference numerals as above. Handpiece 104 includes a housing 152 with an end cap 154 that exhibits an electrical socket 156 through which connections are made to leads 128 and 130 (FIGS. 1, 4, and 5). End cap 154 also has an outlet port or coupling 158 for the aspiration of disrupted tissue. A distal end of the instrument includes a sheath 160 having a port or connector 162 for attachment of an irrigation tube (not shown).

In an alternative embodiment (not illustrated), the connection to ground is established through the hand piece cable (connected at 156) via a conductor that is electrically connected to the applied circuit. In that case, electrical socket 156 forms the connector that enables grounding of the probe 106, as well as the generation of the ultrasonic standing wave in the probe. The wire or cable 116 is then connected to the instrument via electrical socket 156.

Figure 6:
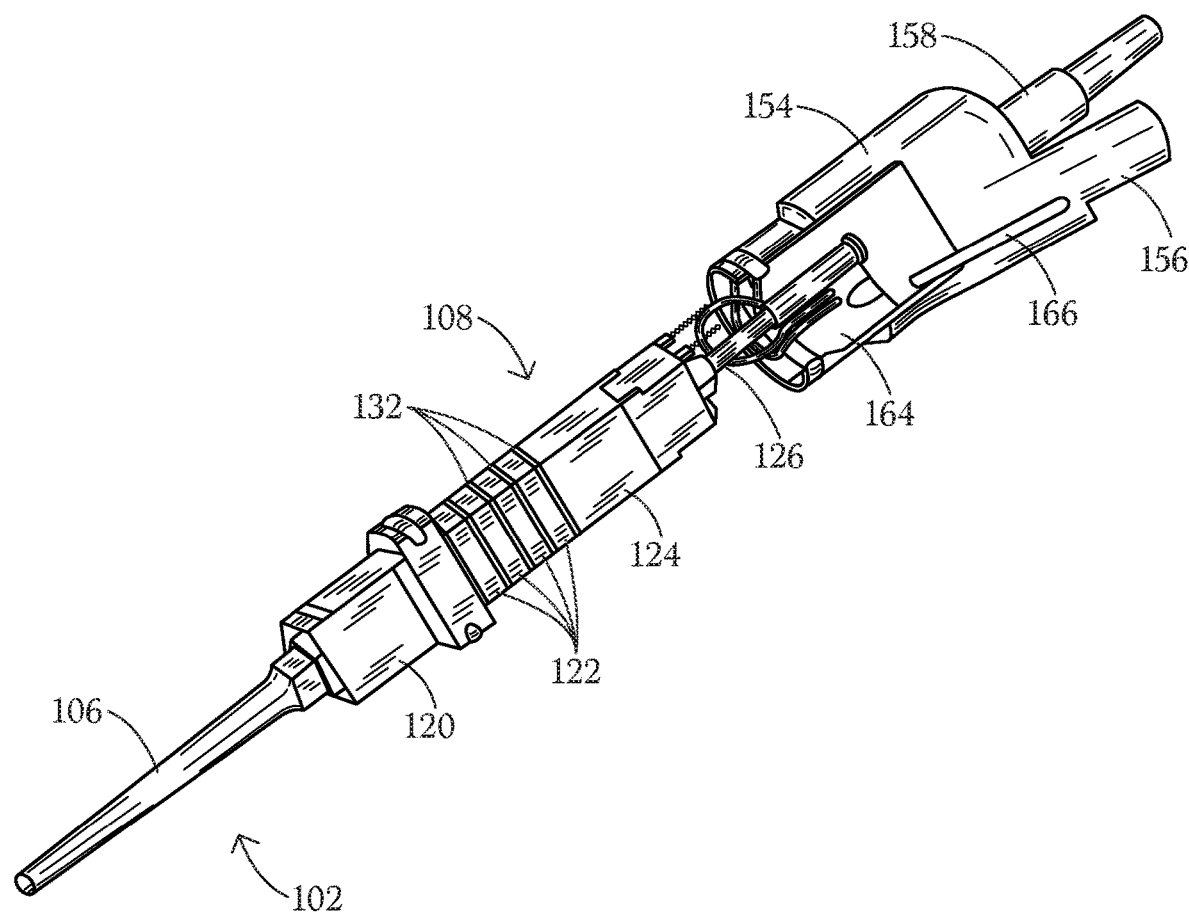
FIG. 6 is partially an isometric view and partially a longitudinal or axis cross-sectional view of the instrument of FIGS. 3-5.
Figure 7:
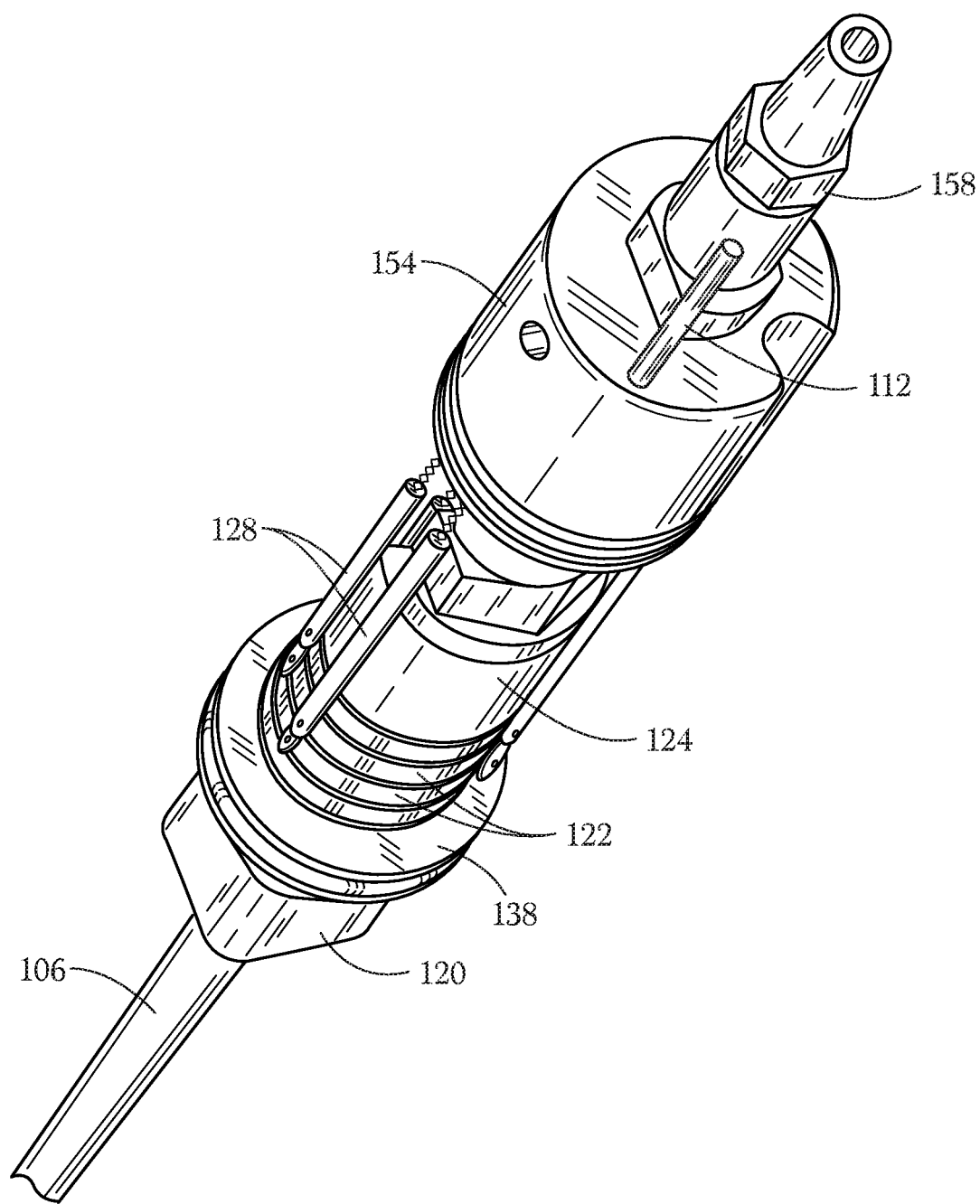
FIG. 7 is an isometric rear and side view of the instrument of FIGS. 3-6.

FIG. 6 shows end cap 154 slightly removed in a proximal direction. End cap 154 is provided internally with a metal liner 164 that is mechanically and electrically connected to an extension of bolt 126. Liner 164 fits over and may engage rear driver 124. Liner 164 has a rearwardly extending metal finger 166 that serves as connector or spud 112 (see also FIG. 7) at its outer end.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An ultrasonic surgical device comprising:
a hand piece;
an electromechanical transducer assembly disposed inside said hand piece, said transducer assembly being configured for converting electrical waveform energy of an ultrasonic frequency into ultrasonic vibratory energy;
a probe mounted to a distal end of said hand piece, said probe being operatively connected to said transducer assembly;
an electrical connector mounted at least indirectly to said hand piece;
an electrical circuit electrically connecting said probe to said connector; and
a wire or cable operatively coupled at one end to said electrical connector and at an opposite end to electrical ground and configured to electrically ground said probe and thereby reduce or prevent current flow through or along said probe to a patient.

2. The surgical device defined in claim 1 wherein said transducer assembly includes a front driver, a stack of piezoelectric disks, a rear driver, and a bolt connecting said rear driver to said front driver, said electrical circuit including said front driver, said bolt and said rear driver.

3. The surgical device defined in claim 2 wherein said stack of piezoelectric disks is a floating stack.

4. The surgical device defined in claim 2 wherein said hand piece has an end cap at a proximal end, said end cap including a metal liner, said metal liner including a projecting finger that extends to said electrical connector, said electrical circuit further including said metal liner and said projecting finger.

5. A method for using an ultrasonic surgical device including:
a hand piece;
an electromechanical transducer assembly disposed inside said hand piece, said transducer assembly being configured for converting electrical waveform energy of an ultrasonic frequency into ultrasonic vibratory energy;
a probe mounted to a distal end of said hand piece, said probe being operatively connected to said transducer assembly;
an electrical connector mounted at least indirectly to said hand piece;
an electrical circuit electrically connecting said probe to said connector,
the method comprising:
providing a wire or cable;
operatively coupling one end of said wire or cable to said electrical connector and an opposite end to electrical ground in a configuration adapted to electrically ground said probe and thereby reduce or prevent current flow through or along said probe to a patient;
placing an operating tip of said probe in contact with organic tissue of a patient;
while said operating tip is in contact with the organic tissue, conducting an alternating voltage to said transducer assembly to induce same to generate a mechanical standing wave of ultrasonic frequency in said probe; and
while said operating tip is in contact with the organic tissue, conducting leakage current away from said probe to ground via said electrical circuit, said connector and said wire or cable and preventing current from flowing through or along said probe to the organic tissue of the patient.

6. The method defined in claim 5, further comprising providing an intraoperative neurophysiological monitoring device, operatively connecting said intraoperative neurophysiological monitoring device to the patient proximate a point of contact of said operating tip of said probe with the organic tissue of the patient, and operating said intraoperative neurophysiological monitoring device to detect neuron activation.

* * * * *